US00PP23106P2

(12) United States Plant Patent
Zaiger et al.

(10) Patent No.: US PP23,106 P2
(45) Date of Patent: Oct. 16, 2012

(54) INTERSPECIFIC TREE NAMED 'BELLA JEWEL'

(50) Latin Name: ***Interspecific Prunus* species**
Varietal Denomination: Bella Jewel

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 13/135,385

(22) Filed: Jul. 5, 2011

(51) Int. Cl.
*A01H 5/00* (2006.01)

(52) U.S. Cl. ..... Plt./180

(58) Field of Classification Search ..... Plt./180
See application file for complete search history.

*Primary Examiner* — Kent L Bell

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with vigorous upright growth.
2. Heavy and regular production of fruit.
3. Fruit with dark red flesh.
4. Fruit with very good flavor and eating quality.
5. Fruit with an attractive red skin color.

1 Drawing Sheet

Botanical classification: Interspecific *Prunus* species.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of interspecifics and proprietary interspecifics, which are known to us, and mentioned herein, 'Dapple Fire' Interspecific (U.S. Plant Pat. No. 12,409), 'Flavor Grenade' Interspecific (U.S. Plant Pat. No. 12,097), 'Candy Stripe' Interspecific (U.S. Plant Pat. No. 17,828), 'Bella Sun' Interspecific (U.S. Plant Pat. No. 21,817), 'Bella Royale' Interspecific (U.S. Plant Pat. No. 19,925) and the proprietary interspecific seedlings '279LV182' and '63EG32'.

STATEMENT REGARDING FEDERALLY SPONSORED RESEARCH AND DEVELOPMENT

Not applicable.

ORIGIN OF THE VARIETY

The new and distinct variety of interspecific tree was originated by us from crosses of the following species; *Prunus salicina*, (*Prunus salicina*×*Prunus persica* var. *nucipersica*), *Prunus persica*, (*Prunus salicina*×*Prunus armeniaca*) and *Prunus armeniaca*. The present variety is a first generation cross between the proprietary interspecific seedling with the field identification number '279LV182' and 'Bella Sun' Interspecific (U.S. Plant Pat. No. 21,817). The seed parent ('279LV182') was developed by us from crosses of the following, the proprietary interspecific selection '63EG32', 'Dapple Fire' Interspecific (U.S. Plant Pat. No. 12,409), 'Flavor Grenade' Interspecific (U.S. Plant Pat. No. 12,097) and 'Candy Stripe' Interspecific (U.S. Plant Pat. No. 17,828). A large number of these first generation seedlings, growing on their own root system, were budded to older trees of 'Nemaguard' Rootstock (non-patented) to induce earlier fruit production for evaluation. Under close and careful observation one seedling, which is the present variety, exhibited desirable fruit and tree characteristics and was selected in 2009 for additional asexual propagation and commercialization.

ASEXUAL REPRODUCTION OF THE VARIETY

Additional asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new and distinct variety of interspecific tree [Plum, (Plum×nectarine), peach, plumcot and cot], is of large size, vigorous upright growth and a productive and regular bearer of medium to large size, red flesh fruit with very good flavor and eating quality. The fruit is further characterized by having attractive red skin that has very short, soft pubescence similar to an apricot. In comparison to the seed parent ('279LV182') the fruit of the new variety has darker red skin color and is approximately 14 days earlier in maturity. In comparison to its pollen parent 'Bella Sun' Interspecific (U.S. Plant Pat. No. 21,817) the fruit of the new variety has red skin and flesh compared to yellow and is larger in size. In comparison to the commercial interspecific variety 'Bella Royale' (U.S. Plant Pat. No. 19,925) the fruit of the new variety has darker red skin color, red flesh compared to yellow, is larger in size and is approximately 7 weeks earlier in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 4 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 4 year old specimens grown near Modesto, Calif., with color in accordance with Munsell Book of Color.

Tree:

*Size*.—Large, pruned to 3 to 3.5 meters in height and width for economical harvesting of fruit. Varies with different cultural practices and climatic conditions.

*Vigor*.—Vigorous, tree growth of approximately 1.5 to 2 meters in height the first growing season.

*Form*.—Upright, usually pruned to vase shape.

*Branching habit*.—Upright, crotch angle approximately 35°, increases with heavy crop load.

*Productivity*.—Productive, thinning and spacing of fruit necessary for desired market size fruit.

*Bearer*.—Regular, adequate fruit set, no alternate bearing observed.

*Fertility*.—Self-sterile, pollinator required.

*Density*.—Medium dense, usually pruned to vase shape to allow sunlight to center of tree to enhance fruit color and health of fruit spurs.

*Hardiness*.—Hardy in all stone fruit growing areas of California. Tree grown in USDA Hardiness Zone 9. Winter chilling requirement approximately 450 hours at or below 45° F.

Trunk:

*Size*.—Average circumference 25.4 cm at 38.1 cm above ground on a 4 year old tree.

*Stocky*.—Medium stocky.

*Texture*.—Medium shaggy, roughness increases with age of tree.

*Color*.—Varies from 2.5Y 5/2 to 2.5Y 4/2.

Branches:

*Size*.—Medium. Average circumference 10.2 cm at 1.2 meters above ground on a 4 year old tree. Crotch angle approximately 35° increases with heavy crop load.

*Surface texture*. —New growth relatively smooth. Mature growth medium rough, roughness increases with age.

*Lenticels*.—Average number 13 in a 25.8 square cm surface of branch. Average length 3.0 mm. Average width 0.9 mm. Color varies from 10YR 7/8 to 10YR 6/8.

*Color*.—New growth varies from 2.5GY 6/8 with 5R 4/6 where exposed to the sun. Mature growth 10YR 3/2, varies with age of growth.

Leaves:

*Size*.—Small to medium. Average length 74.1 mm. Average width 35.7 mm.

*Form*.—Oblanceolate.

*Apex*.—Acuminate.

*Base*.—Cuneate.

*Margin*.—Doubly serrate.

*Thickness*.—Medium.

*Surface texture*.—Upper surface relatively smooth, slight indentations over midrib and leaf veins, glabrous. Lower surface relatively smooth, except for small ridges created by midrib and pinnate venation, glabrous.

*Petiole*.—Average length 9.2 mm. Average width 1.9 mm. Longitudinally grooved. Color varies from 5GY 7/6 with 5R 3/6. Surface — pubescent, very short in length.

*Glands*.—Type — globose. Size — small. Average length 0.9 mm. Average diameter 0.5 mm. Average number 3, varies from 2 to 4. Located primarily on the base of the leaf blade and upper portion of the petiole. Color — 2.5GY 6/6.

*Stipules*.—Present. Average length 5.0 mm. Edges — serrate. Color — varies from 5GY 6/6 to 5R 3/6.

*Color*.—Upper surface varies from 5GY 4/8 to 7.5GY 3/4. Lower surface varies from 5GY 5/4 to 7.5GY 5/4. Midrib color varies from 2.5GY 7/6 to 5GY 7/6.

Flower buds:

*Size*.—Small to medium. Average length 11.2 mm. Average diameter 5.4 mm.

*Hardiness*.—Hardy with respect to California winters.

*Form*.—Conical, becoming elongated before opening.

*Pedicel*.—Average length 8.6 mm. Average width 0.9 mm. Color varies from 2.5GY 7/6 to 5GY 7/6. Surface — glabrous.

*Color*.—N 9.5/ (white).

*Number of buds per spur*.—Average number 10, varies from 5 to 12. Varies with age of spur.

Flowers:

*Blooming period*.—Date of First Bloom Feb. 19, 2011. Date of Petal Fall Mar. 1, 2011, varies slightly with climatic conditions.

*Size*.—Medium. Average length 12.9 mm. Average diameter 19.3 mm.

*Petals*.—Size— medium. Number — normally 5, alternately arranged to sepals. Average length 12.1 mm. Average width 7.6 mm. Form — obovate. Margin — entire. Color — N 9.5/ (white). Both upper and lower surfaces glabrous.

*Sepals*.—Size — small. Number — normally 5, alternately arranged to petals. Average length 3.4 mm. Average width 2.8 mm. Form — triangular, apex rounded. Margin — entire. Color — upper surface varies from 5GY 6/6 to 5GY 5/6. Lower surface varies from 2.5GY 6/6 to 5GY 5/6. Both upper and lower surfaces glabrous.

*Stamens*.—Average number per flower 37. Average filament length 8.9 mm. Filament color N 9.5/ (white). Anther color varies from 5Y 8/8 to 5Y 8/10.

*Pollen*.—Self sterile, pollinator required. Color varies from 2.5Y 7/12 to 5Y 7/12.

*Pistil*.—Normally one. Surface — pubescent. Average length 9.9 mm. Stigma height approximately 1.5 mm below anthers. Color varies from 10Y 8/6 to 2.5GY 8/6.

*Fragrance*.—Heavy aroma.

*Color*.—N 9.5/ (white).

*Number flowers per flower bud*.—Average number 3, varies from 1 to 4.

*Pedicel*.—Average length 9.8 mm. Average width 1.0 mm. Color varies from 2.5GY 7/6 to 2.5GY 7/8. Surface — glabrous.

Fruit:

*Maturity when described*.—Firm ripe.

*Date of first picking*.—Jun. 9, 2011.

*Date of last picking*.—Jun. 17, 2011, varies slightly with climatic conditions.

*Size*.—Medium to large. Average diameter axially 62.6 mm. Average transversely in suture plane 57.3 mm. Average weight 125.0 grams, varies slightly with fertility of the soil, amount of thinning and climatic conditions.

*Form*.—Globose to slightly elongated.

*Suture*.—Nearly smooth, extends from base to apex.

*Ventral surface*.—Nearly smooth.

*Apex*.—Nearly rounded.

*Base*.—Rounded to slightly retuse.

*Stem cavity*.—Rounded to slightly elongated in the suture plane. Average depth 2.6 mm. Average diameter 3.7 mm.

Stem:

*Size*.—Medium. Average length 16.8 mm. Average diameter 2.6 mm.

*Color*.—Varies from 7.5YR 4/6 to 10YR 3/4.

Flesh:

*Ripens*.—Evenly.

*Texture*.—Firm, smooth texture.

*Fibers*.—Few, small, tender.

*Firmness*.—Good, comparable to other commercial interspecifics.

*Aroma*.—Moderate.

*Amydgalin*.—Undetected.

*Eating quality*.—Very good.

*Flavor*.—Very good, good balance between acid and sugar.

*Juice*.—Moderate amount, enhances flavor.

*Brix*.—Average of 18.0° Brix, varies slightly with amount of fruit per tree and climatic conditions.

*Color*.—Varies from 5R 3/8 to 7.5R 2/8. Pit cavity 5R 2/4.

*Stone cavity*.—Average length 21.5 mm. Average width 19.0 mm. Average depth 5.0 mm.

Skin:

*Thickness*.—Medium.

*Surface*.—Smooth.

*Pubescence*.—Moderate amount, very short.

*Bloom*.—Moderate amount, completely covered.

*Tendency to crack*.—Very slight.

*Color*.—Ground color varies from 7.5Y 8.5/4 to 10Y 8/4. Overspread with 5R 2/4.

*Tenacity*.—Tenacious to flesh.

*Astringency*.—Undetected.

Stone:

*Type*.—Clingstone.

*Size*.—Medium. Average length 21.0 mm. Average width 18.5 mm. Average thickness 9.6 mm.

*Form*.—Ovoid.

*Base*.—Varies from flat to slightly rounded.

*Apex*.—Slightly pointed. Average length 0.8 mm.

*Surface*.—Slightly pitted throughout, one short groove on each side of suture extending from base toward apex.

*Sides*.—Unequal, one side extending slightly further from suture plane.

*Ridges*.—One short small ridge on each side of suture extending from base to apex.

*Tendency to split*.—None.

*Color*.—Varies from 7.5YR 6/6 to 10YR 6/6 when dry.

Kernel:

*Size*.—Medium. Average length 13.9 mm. Average width 9.8 mm. Average depth 5.7 mm.

*Form*.—Ovate.

*Viability*.—Viable, complete embryo development.

*Skin color*.—Varies from 5Y 9/4 to 7.5Y 9/4.

Use:

*Dessert*.—Market — local and long distance.

Keeping quality: Good, held firm in cold storage for 21 days at 38° to 42° F. without internal breakdown of flesh or appreciable loss of flavor.

Shipping quality: Good, minimal flesh bruising or skin scarring during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

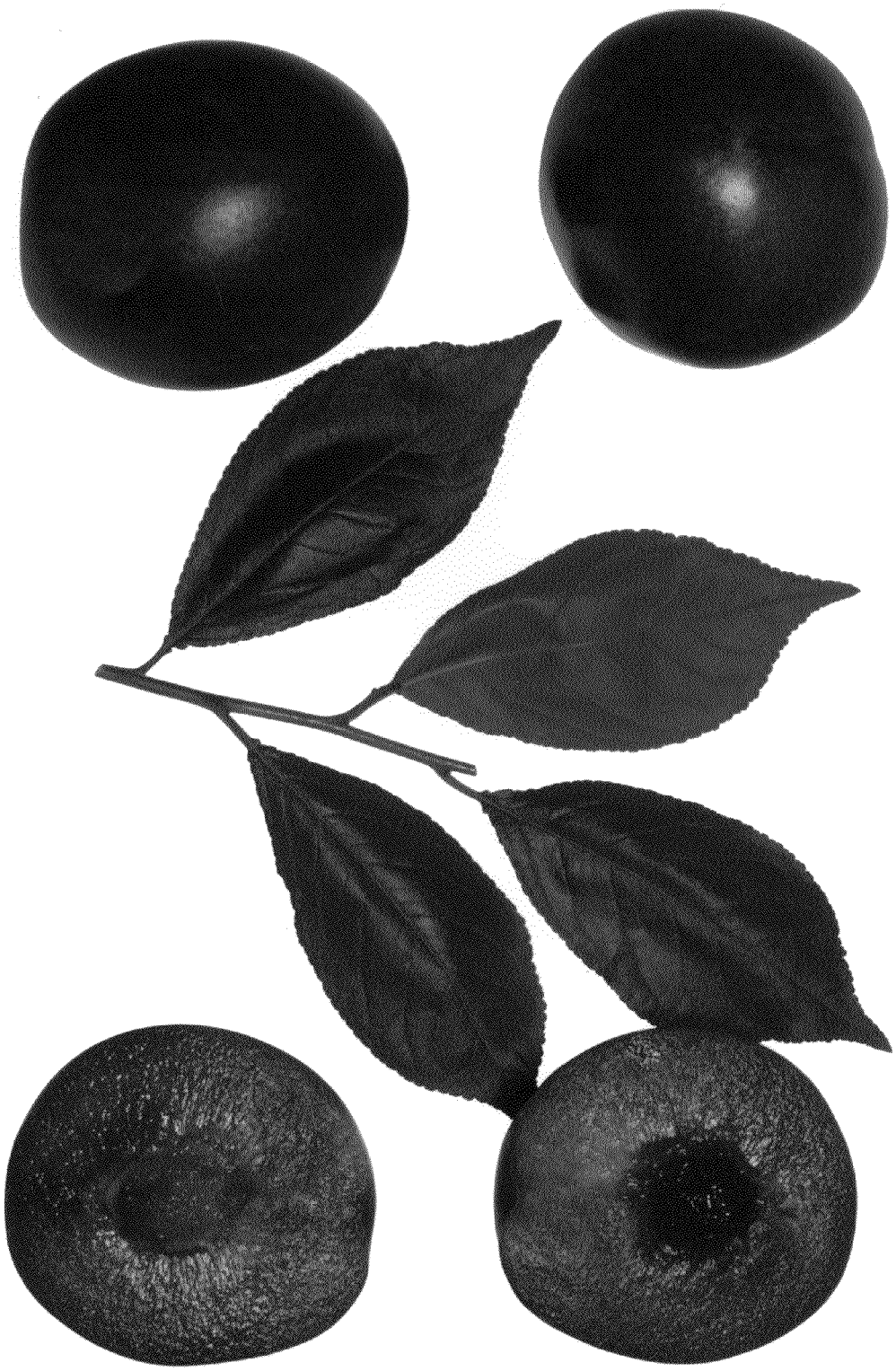

* * * * *